(12) United States Patent
Cardarelli

(10) Patent No.: US 6,619,955 B2
(45) Date of Patent: Sep. 16, 2003

(54) DENTAL MIRROR DEVICE

(76) Inventor: Venanzio Cardarelli, 20 N. Triangle Dr., Plymouth, MA (US) 02360

( * ) Notice: Subject to any disclaimer, the term of this patent is extended or adjusted under 35 U.S.C. 154(b) by 34 days.

(21) Appl. No.: 10/050,984

(22) Filed: Jan. 18, 2002

(65) Prior Publication Data

US 2002/0098461 A1 Jul. 25, 2002

Related U.S. Application Data

(60) Provisional application No. 60/262,679, filed on Jan. 22, 2001.

(51) Int. Cl.[7] ................................................. A61B 1/24
(52) U.S. Cl. ........................................ 433/30; 359/875
(58) Field of Search ..................... 433/30, 31; 600/189, 600/247, 248; 359/872, 875, 882; 362/139

(56) References Cited

U.S. PATENT DOCUMENTS

| | | | | |
|---|---|---|---|---|
| 159,836 A | * | 2/1875 | Osborn | 433/30 |
| 695,338 A | * | 3/1902 | Paynter et al. | 362/139 |
| 849,209 A | * | 4/1907 | Crawford | 600/248 |
| 1,397,090 A | * | 11/1921 | Dimas | 433/30 |
| 1,500,798 A | * | 7/1924 | Campodonico | 433/31 |
| 2,679,103 A | * | 5/1954 | Erickson | 433/31 |
| 3,988,058 A | * | 10/1976 | Chaney et al. | 359/880 |
| 4,277,140 A | * | 7/1981 | Manzoni | 350/288 |
| 4,405,302 A | * | 9/1983 | Lewis | 433/30 |
| 5,230,622 A | * | 7/1993 | Brossoit | 433/31 |
| 5,458,486 A | | 10/1995 | Ballard | 433/30 |

* cited by examiner

*Primary Examiner*—John J. Wilson
(74) *Attorney, Agent, or Firm*—D. Michael Burns

(57) ABSTRACT

A dental mirror having a planar surface encircled by a beveled perimeter. The mirror rotatively mounted upon a spherical support ball, whereby the dentist can continually maintain the correct angle of incidence to capture and reflect light beams from a light source. The planar surface continually being capable of pivoting in relationship to the pressure by the dentist to provide the smallest angle of incidence of reflecting light beams, which is vital to securing the greatest amount of illumination to the surgical area and also in avoiding unwanted distortion of any images in the work area.

11 Claims, 4 Drawing Sheets

DENTAL MIRROR DEVICE

CROSS REFERENCE TO RELATED APPLICATION

This application is based on Provisional Patent Application Serial No. 60/262,679 filed Jan. 22, 2001.

BACKGROUND OF THE INVENTION

1. Field of the Invention

The present invention relates to a dental mirror device that is designed to more efficiently deflect light to the surgical field during dental procedures and more specifically to a dental mirror that can be angulated by the dentist, assistant or dental hygienist, to aid in indirect vision as well as the deflection of the light beam and the retraction of tissues. The three primary functions of the dental mirror will be indirect vision, deflection of light and the retraction of tissues.

2. Description of the Prior Art

The oral cavity is an extremely difficult area in which to work. Vision and access are impaired by the lips, cheek, tongue, and the patient's ability to open the mouth. Restorative care must be accomplished with extreme care as to not injure the soft tissue structures. To achieve this, retraction of such tissues will be necessary. The devices that are available and which can be used by the dental team are the dental mirror, rubber dam, cotton holders, retraction, suction lines and bite blocks. The dental mirror is the most frequently used of the above devices. When the dental mirror is being used for retraction by the assistant or dentist, the dentist is usually using direct vision. This is the actual viewing of the surgical field utilizing the dental unit light as well as the operatory ceiling light. The combination of these light beams is sufficient for operating purposes as well as to hopefully preventing eye damage, strain and fatigue.

The dental mirror takes on its most important functions when we use it in combinations of the illumination of the surgical field as well as indirect vision. Indirect vision is the viewing of the surgical field through the mirror image of the field. Different from the direct vision system is that in the indirect, both the operatory light as well as the dental unit light are hopefully being captured by the dental mirror such that it may be angulated or deflected to illuminate the surgical field. While this is being achieved, the dentist or hygienist are positioning the mirror to have proper visual image of the site through the mirror.

In the prior art the dentist accomplishes the above by a fixed handle connection to a pre-set 30° to 40° angle circular mirror head. The present invention is designed to provide increased angular capabilities for: better mirror image; to provide a more abundant and useful deflected beam of light to the field; and to place less strain and fatigue on the dentist/hygienist hands, finger, neck and back. The present invention also takes into account weight distribution, autoclavability, disposability, cost factor, handling ability and its relational benefits to better vision and better field of illumination.

The prior art in U.S. Pat. No. 5,458,486 issued to Ballard on Oct. 17, 1995, shows a mirror apparatus that teaches the need for adjusting the position of the mirror relative to the working area. This inventor discusses methods of bending, twisting and flexing the handle and shaft while also using a ball bearing design to not only affix the mirror to the shaft but to provide a greater range of self-adjustment for mirror angulation. Other prior art patents attempt to solve the problem of directing light beams to the work area is a similar fashion by focusing upon the articulation of the handle and shaft.

None of the above inventions and Patents, taken either singly or in combination, is given to describe the instant invention as claimed.

SUMMARY OF THE INVENTION

Accordingly, the above problems and difficulties are obviated by the present invention which provides for a dental mirror device which is positionable within a patient's mouth by a dentist. The apparatus includes a handle portion, a shank portion and a mirror housing. The mirror housing is attached to the shank in such a way that it is capable of being angulated to capture specular reflection and also to direct the reflected beams towards the surgical field. The angulation also aids in image reflection. It is preferred that the mirror surface be planar (flat) to insure that the image is the same size as the object. In dental procedures, it is critical that the image reflected be the same size, in order that the dentist may see the situation the way it is.

The present invention provides the dentist with the ability to control the angulation of the mirror so that the angle of incidence is equal to the angle of reflection. The light beam is reflected when it hits the surface of the mirror. The angle in which the beam strikes the surface is the angle with which it is reflected back. The incident ray/beam approaches the mirror with as small an angle as possible, thereby giving the sharpest possible reflective angle. This is the most desired illumination of the surgical field.

The present invention can utilize a variety of handles whether they be conventionally shaped, ergonomically designed, diposable, metal, or plastic. The handle may be reusable and the mirror disposable. The key is that the mirror have the ability to angulate so that the smallest angle of incidence is provided, regardless of whether the mirror is being used in a retractory fashion.

One object of the invention is that the mirror have the ability wherein the planar surface of the mirror will have 360 degrees of rotation and the ability to be angulated at any degree.

Another object of the present invention is that the mirror portion of the device be easily installed to the shank portion of the device, and easily removed for disposal or autoclaving.

A still further object of the present invention is that the mirror portion provides for a pre-set desired angular deviation, thereby preventing displacement of the mirror while in use.

Another object of the present invention is to allow the control of the angle of incidence or at least restrict it to a maximum deviation.

DETAILED DESCRIPTION OF THE PREFERRED EMBODIMENT

Figure 1:
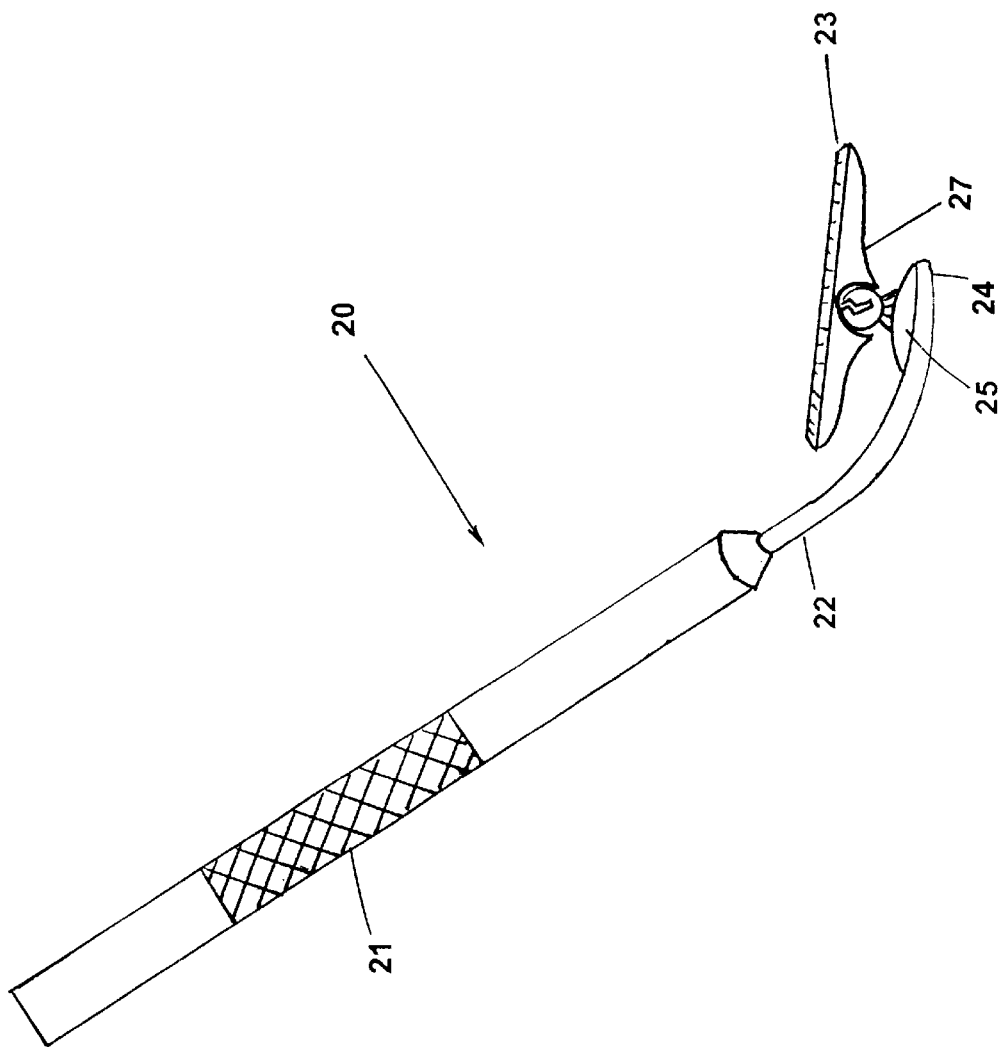
FIG. 1 is a view partly in elevation and partly in section illustrating the whole structure of the planar mirror.

For the purposes of promoting an understanding of the principles of the invention, reference will now be made to the embodiments illustrated in the drawings and specific language that will be used to describe the same. It will never the less be understood that no limitation of the scope of the invention is thereby intended, such alterations and further modifications in the illustrated device, and such further application of the principles of the invention as illustrated therein being contemplated as would normally occur to one skilled in the art to which the invention relates.

Figure 2:
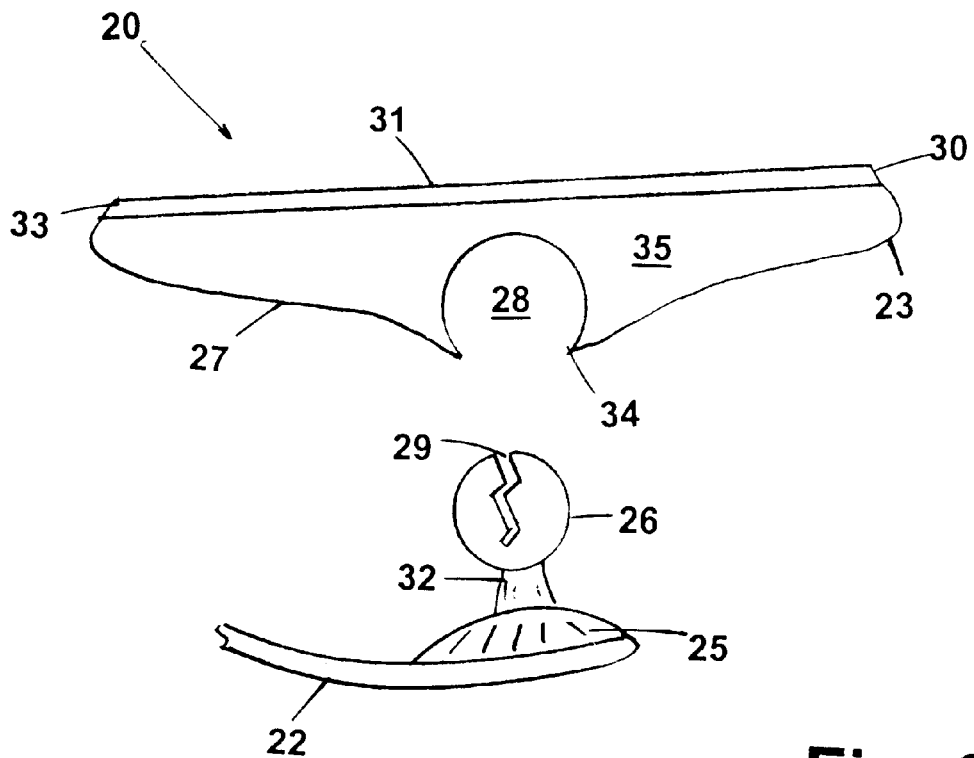
FIG. 2 is an expanded view of the side of the planar mirror portion and base section of shank portion.

Referring to FIGS. 1–2, a dental mirror device 20 is illustrated which can be placed in a patient's mouth. The device 20 includes a handle portion 21, a shank portion 22, and a mirror housing 23. Handle portion 21 can take many forms and shapes from angulated to ergonomic without deviating from the inventive concept. For the present purposes the handle portion 21 is shown as a conventional dental mirror handle. The dentist or hygienist may manually angulate the handle to a workable position in the patient's mouth such that the incident (ray/beam) approaches the mirror with as small an angle as possible, thereby giving a reflective angle equal in degrees to the angle of incidence for the best illumination of the work area as well as the proper mirror image of the object or surgical site.

The prior art teaches of handles that connect to the shanks in a variety of ways. Some are screwed together or have some other manner of connecting to each other. Others are all one piece. Some are made from metals that can be autoclaved while others are made from disposable plastics. In most cases, it is the mirror housing that is the most difficult to sterilize, therefore it is often disposable. The present invention can utilize numerous configurations, however the inventive concept involves the manner in which the mirror portion 23 relates to the distal end 24 of the shank portion 22, which has disposed therein a generally circular base section 25. A spherically shaped ball 26 can then be screwed into the base section 25, or be fabricated as a molded piece. Base section 25 creates a 360° constriction with the bottom section 27 of mirror housing 23. Mirror housing 23 being of a generally circular shape, having a generally spherical shaped recess 28 in bottom support section 27. Recess 28 being of sufficient size and shape to accept ball 26, thereby releasably connecting mirror housing 23 to shank portion 22. To aid in the mating process of ball 26 to recess 28, ball 26 has a split center construction creating a pair of resilient semi-spheres with a crevice 29 defined between them. When ball 26 is inserted into recess 28 the semi-spheres are compressed together and when seated within recess 28 biasly spring apart to create a tight friction fit therein. Mirror housing 23 now being easily removed for autoclaving or disposal. Mirror housing 23 having a top support section 30 comprising of a generally circular reflective planar mirror 31 made of glass, although highly polished metal can also be used to reflect light. When mirror housing 23 is in position, the planar (flat) mirror 31 can be angulated in 360° and can only be restricted by contact between the inner edge 34 of the recess 28 and the circular restriction area 32. It is highly desirable for the mirror surface 31 to be planar so that specular reflection is captured and the image is the same size as the object. Also, to avoid the distortion that occurs with the use of mirrors that are concave or convex. As previously stated the most useful reflective light is that which occurs at the smallest angle of incidence. The external perimeter of the top section 30 has a circular external bevel area 33 which holds the planar mirror surface 31. With the mirror 31 rotating upon ball 26 for a full 360°, the dentist will be able to better direct the reflective light beams to the smallest angle of incidence. If desired to reduce weight at the distal end of the device, the mirror portion can have an internal void 35 between top and bottom sections 30 and 27.

Figure 3:
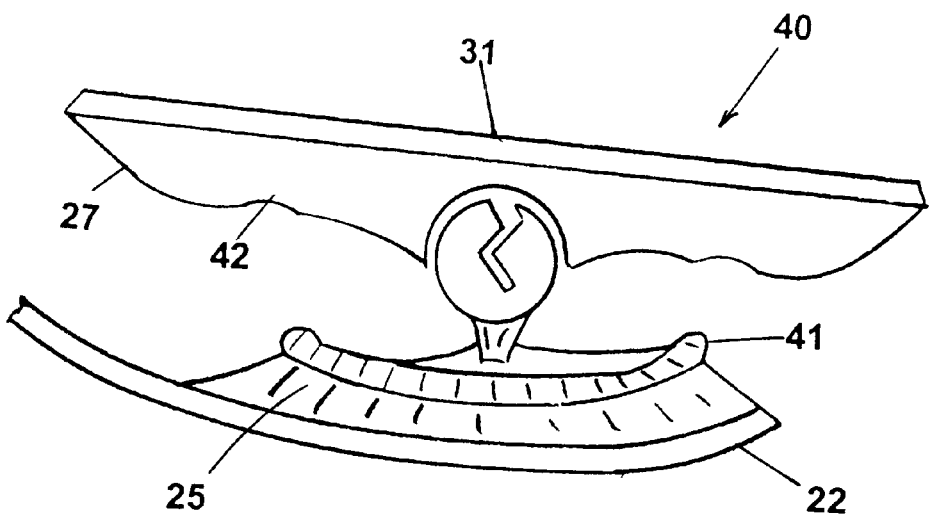
FIG. 3 is an elevational view showing a partially cross section portion of an alternate embodiment having a fixed angular deviation.

The present invention can be modified slightly as shown in FIG. 3 to provide an alternative embodiment 40 which would provide a raised circular ring 41 about the support base 25 to limit the angular deviation to a more precise displacement of mirror housing 23. This alternative embodiment 40 employs a support base 41 having the same spherical ball 26 design as in the preferred embodiment 20 and the same design features at the top section 30 of the mirror housing 23 with the exception of the bottom section 27 of mirror portion 23. A circular channel 42 is defined in the bottom section 27. The channel of size and shape to receive the raised ring 41 in a friction-fit. Upon the mirror housing 23 rotating about the ball 26, the ring 41 will serve to restrict the amount of tilt and the mating of ring 41 and channel 42 will serve to secure the same.

Figure 4:
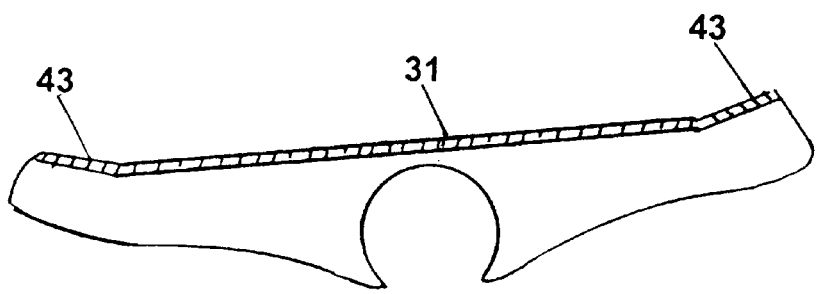
FIG. 4 is an elevational sectional view of an alternate embodiment of the planar mirror wherein the outer area of the mirror is angled.

A modification to the planar mirror surface 31 is shown in FIG. 4, wherein the perimeter has an outer angular mirror 43 added to the inside of the perimeter. The outer perimeter 33 still being beveled to confine the mirror 31 from being dislodged. The angle of the outer mirror 43 being minimal as the slight elevation is necessary to capture more light for illumination of the working field as well as the general area. If the angle of the outer mirror 43 is too great then a large portion of light beams will be prevented from ever reaching the mirrored surface 31.

Figure 5:
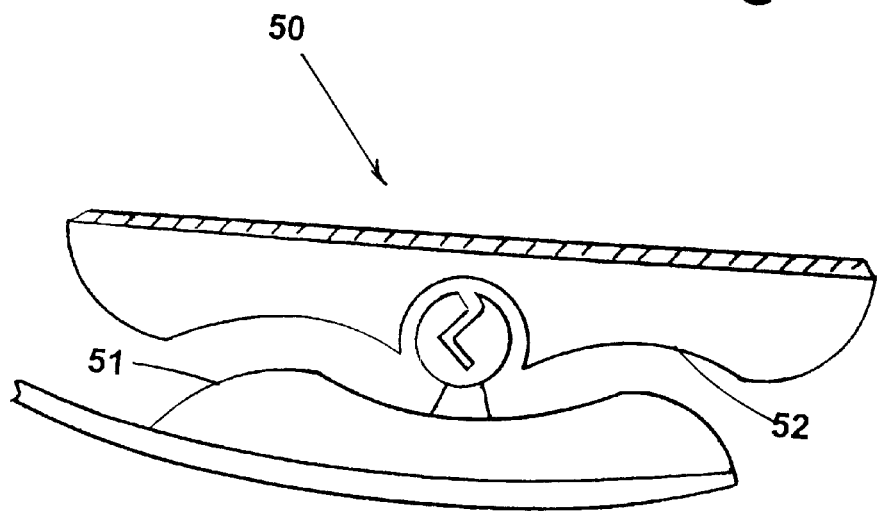
FIG. 5 is an alternative embodient depicting by an elevational sectional view a mirror configuration having a means for limiting the angular deflection.
Figure 6:
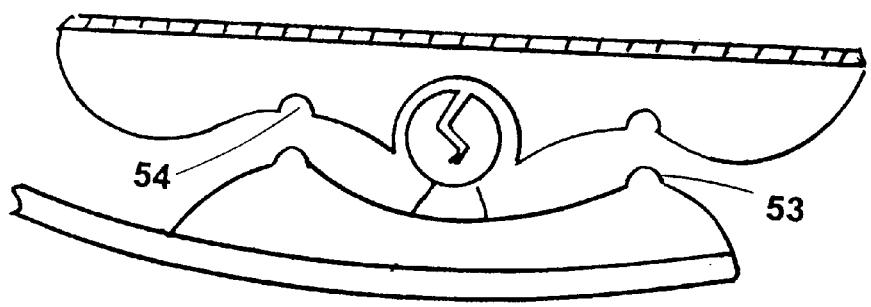
FIG. 6 is an elevational view of FIG. 5 with the addition of a circular ring for snap-fitting the mirror within a 360° area.

Another modification is depicted by FIGS. 5 and 6. FIG. 5 shows a limited angle of deflection mirror 50 which utilizes a base 51 having a rounded convex shape defined to limit the angle of deflection of the mirror housing 23. In this modification the bottom section 27 of the housing 23 has a concave surface 52, which will contact the convex base 51 to thereby restrict the tilt of the mirror housing 23. This modified mirror 50 can be further modified with a circular male positive ridge 53 disposed on the apex of the base 51 which will friction fit with a circular female negative slot 54 to lock the mirror housing 23 at a particular angulation.

Figure 7:
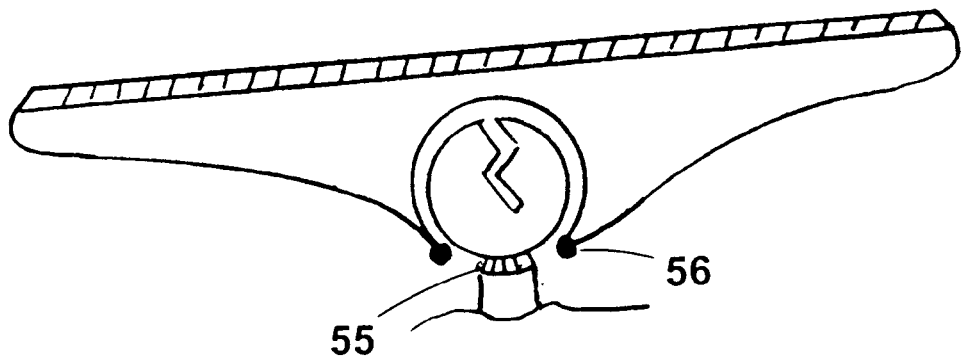
FIG. 7 is an elevational view of an alternative embodiment having a recessed groove in the base section.
Figure 8:
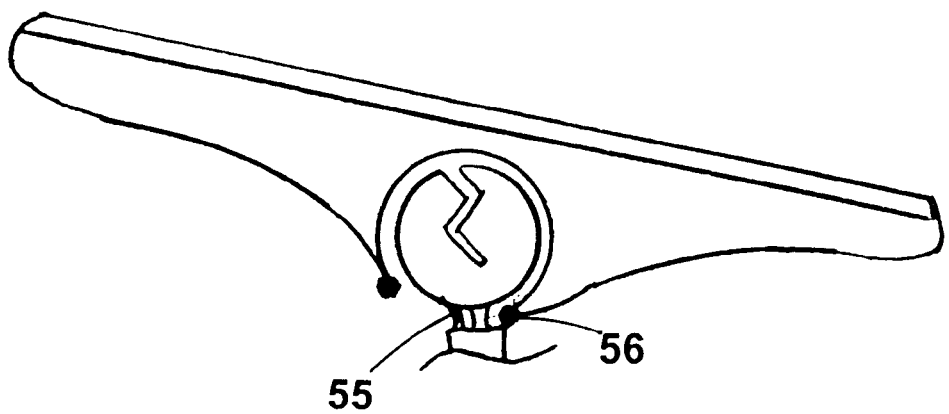
FIG. 8 is an elevational view showing the mirror portion locked into the groove of FIG. 7.

FIGS. 7 and 8 show another modification to the basic preferred embodiment 20. A controlled angle lock is created, not with the base section 25, but by locking into the circular restriction area 32. A recessed groove 55 is defined in the stem of the restriction area 32. The inner edge 34 of the recess 28 has a generally rounded projection 56 which will lock into the recessed groove 55 at the maximum point of mirror deflection. The groove 55 being 360° allows for the mirror housing 23 to spin completely about the ball 26 at this maintained angle. The locking in of the mirror housing 23 in this fashion also prevents it from being inadvertently dislodged.

While there has been described what are presently considered the preferred embodiments of the invention, it will be apparent to those skilled in the art that modifications and changes can be made therein without departing from the scope of the present invention as defined by the appended claims.

I claim:

1. A dental mirror comprising:

a handle portion;

a mirror housing having a bottom support section, the support section having a generally circular shape recess, the recess having an inner edge; and a shank portion having at a distal end a circular base section comprising of a circular restriction area, the base section further having a spherically shaped ball with split center construction for creating a pair of resilient semi-spheres with a crevice defined therebetween, the semi-spheres capable of being compressed together and seated within the recess of the mirror housing, whereby upon release biasly spring apart to create a releasable tight friction fit capable of angulated movement between the mirror housing and the shank portion, whereby, the mirror housing will be free to angulate in a 360 degree direction for maximum reflection of light beams at the smallest angle of incedence, the angulation only restricted by the contact between the inner edge of the recess and the circular restriction area.

2. The dental mirror according to claim 1, wherein the mirror housing comprises:

a top support section having a generally circular reflective planar mirror, the planar mirror being held in place by a beveled top support section perimeter.

3. The dental mirror according to claim 2, wherein the planar mirror is made of glass.

4. The dental mirror according to claim 2, wherein the planar mirror is made of a highly polished metal.

5. The dental mirror according to claim 2, wherein the planar mirror is made of a lexan plastic material.

6. The dental mirror according to claim 2, wherein the support base further includes a raised circular ring and the bottom section of the mirror housing further includes a circular channel defined therein, the circular channel and circular ring in a mating relationship to thereby restrict and secure the mirror angulation.

7. The dental mirror according to claim 2, wherein the top section of the mirror housing further includes an outer angular mirror around the planar mirror at a slight angle with the planar mirror, whereby more light will be captured for increased illumination of the working area.

8. The dental mirror according to claim 2, wherein the angle of tilt of the planar mirror is further restricted by the bottom section of the mirror housing having a concave surface and the support base having convex base.

9. The dental mirror according to claim 8, wherein the concave surface of the mirror housing further having a circular female negative slot and the convex base of the support base further having a circular male positive ridge for friction fitting with the negative slot, thereby allowing the mirror housing to be locked at a particular angulation.

10. The dental mirror according to claim 1, wherein the spherically shaped ball is attached to the base section by a screw.

11. The dental mirror according to claim 1, wherein the spherically shaped ball and the base section are molded as one piece.

* * * * *